United States Patent [19]

Eury

[11] Patent Number: 5,342,621
[45] Date of Patent: Aug. 30, 1994

[54] ANTITHROMBOGENIC SURFACE

[75] Inventor: Robert P. Eury, Cupertino, Calif.

[73] Assignee: Advanced Cardiovascular Systems, Inc., Santa Clara, Calif.

[21] Appl. No.: 945,107

[22] Filed: Sep. 15, 1992

[51] Int. Cl.$^5$ .......................... A61F 2/00; A61K 17/00
[52] U.S. Cl. ...................................... 424/423; 424/426; 424/428; 424/486; 604/265; 604/403
[58] Field of Search ............... 424/486, 450, 426, 428, 424/488, 423; 604/265

[56] References Cited

U.S. PATENT DOCUMENTS

| 4,239,754 | 12/1980 | Sache et al. | 514/772 |
|---|---|---|---|
| 4,241,046 | 12/1980 | Papahadjopoulos et al. | 424/450 |
| 4,348,329 | 9/1982 | Chapman | 260/403 |
| 4,678,660 | 7/1987 | McGary et al. | 424/443 |
| 4,689,386 | 8/1987 | Chapman et al. | 528/71 |
| 4,721,800 | 1/1988 | Chapman et al. | 556/405 |
| 4,792,599 | 12/1988 | Durrani | 528/272 |
| 4,937,369 | 6/1990 | Chapman et al. | 558/166 |
| 5,015,238 | 5/1991 | Solomon et al. | 604/265 |
| 5,061,254 | 10/1991 | Karakelle et al. | 604/265 |
| 5,128,408 | 7/1992 | Tanaka et al. | 525/54.2 |
| 5,135,516 | 8/1992 | Sahatjian et al. | 604/265 |

FOREIGN PATENT DOCUMENTS

| WO87/02684 | 5/1987 | European Pat. Off. | C08K 5/00 |
|---|---|---|---|
| 0452995A2 | 10/1991 | European Pat. Off. | C08K 5/00 |
| 58105759 | 6/1985 | Japan | 604/265 |

Primary Examiner—Thurman K. Page
Assistant Examiner—Peter F. Kulkosky
Attorney, Agent, or Firm—Fulwider, Patton, Lee & Utecht

[57] ABSTRACT

An anticoagulant releasably associated with a cell membrane mimicking substance is incorporated in a biomedical polymer or polymer coating and serves to both prevent the blood from recognizing the polymer as a foreign substance as well as actively interfere in any coagulation process that may occur.

14 Claims, No Drawings

ANTITHROMBOGENIC SURFACE

BACKGROUND OF THE INVENTION

1. Field of the Invention

The present invention pertains to biocompatible, antithrombogenic materials, and more particularly relates to substances that impart antithrombogenic qualities to a biomedical polymer structure or polymer coating.

2. Description of the Prior Art

An increasing amount of medical hardware is being developed that requires certain components or surfaces thereof to come into contact with a patient's blood flow. It is essential that such blood contacting surfaces be as compatible with the blood as possible which requires that measures be taken to prevent or at least minimize the coagulation of blood. Probes, sensors, catheter devices, prostheses and implantable devices all stand to benefit from such enhanced hemocompatibility as excessive coagulation can impair sensitivity and function, can reduce flow and cause further problems downstream.

A number of different approaches have been employed in the past in an effort to address this problem. Certain drugs introduced into the recirculating blood supply have been found to be effective in decreasing or delaying coagulation by targeting and interfering in any one or more of the many complex interrelationships and sub-processes involved in the coagulation process. Heparin is a compound well-known for its ability to prevent clotting and is in fact normally present in blood in small concentrations. By introducing additional heparin into the blood supply, coagulation rates are reduced.

Such approach does however have the inherent disadvantage that relatively high doses of pharmaceutical agents are caused to circulate throughout the entire circulatory system while their effect is required at only a relatively small, localized site. Substantially undesirable side effects may be associated with such drugs and it may be desirable for the blood to retain its ability to coagulate in other parts of the body. This problem has been addressed with some success by incorporating in or applying to the blood contacting surface a substance that releases an anticoagulant for an extended period of time. The anticoagulant concentration is therefore relatively high at precisely the point its effect is most needed while its overall concentration throughout the body remains relatively low if not negligible. Heparin-benzalkonium chloride complex (HBAC) and heparin-tridodecylmethylammonium chloride complex (HTDMAC) have been found relatively effective as anticoagulant releasing agents although each has associated disadvantages. HBAC forms a rather brittle film and releases heparin very slowly. HTDMAC is more flexible but releases heparin at an even slower rate. Antithrombogenic activity decreases as a function of time and eventually completely ceases upon total depletion of the heparin.

Efforts have alternatively been directed towards developing a material which the blood does not recognize as foreign. Failure to properly recognize a foreign substance prevents the triggering of the coagulation process, i.e. proteins are not deposited on such foreign substance, red blood cells are not destroyed nor become adhered thereto, while platelet aggregation and adhesion also fails to take place. This has been achieved to a limited degree by selecting or synthesizing substances that mimic critical surface characteristics of cell membranes. Cell membranes generally comprise an asymmetrical lipid matrix of polar lipids in which certain specific functional groups are arranged on the outer surface. Synthetic polymer formulations that incorporate similar lipids having similar functional groups have been found to exhibit some antithrombogenic characteristics. Phosphatidylcholine has been found to impart some antithrombogenicity to materials in which it is incorporated.

Although both of the above described approaches do provide some antithrombogenic effects, each is plagued with substantial inherent limitations. Moreover, far greater antithrombogenicity than is currently available is needed, or would be desirable in many biomedical applications.

SUMMARY OF THE INVENTION

The present invention provides a material with which biomedical polymers are rendered substantially more antithrombogenic than has heretofore been achievable. By employing a material that both mimics the structure of the cell membrane and that is additionally capable of carrying and gradually releasing an anticoagulant, significant improvement in antithrombogenicity is realized. Moreover, due to the inherent property of the carrier, the biomedical polymer or coating continues to exhibit a residual degree of antithrombogenicity upon depletion of the anticoagulant.

Phosphatidylcholine (PTC) has been well recognized for its ability to cause a polymer to mimic the surface characteristics of a cell membrane. It has now additionally been found that heparin readily forms an ionic complex with PTC and that such complex, heparin-phosphatidylcholine (HPTC), is easily either directly incorporated in the polymeric structure of a medical device or in a polymer with which selected components of the device are coated or alternatively, may be applied directly to a surface. Moreover, it has been found that the HPTC releases heparin at a much faster rate than the heretofore used HBAC or HTDMAC. This system provides a surface that the blood not only has difficulty in recognizing as a foreign body but one that additionally actively interferes in the coagulation process.

HPTC is readily incorporated directly in biomedical polymers such as polyurethanes, nylon and polycarbonates, and additionally functions as a plasticizer. Alternatively, HPTC is incorporated in a film-forming polymer coating at levels of 35% HPTC and greater that adheres to a large variety of different materials including polymers and metals. Such film forming polymers may further be selected to be biodegradable. HPTC by itself is a relatively soft and pliable substance that is also directly applicable to a variety of materials.

These and other features and advantages of the present invention will become apparent from the following detailed description of preferred embodiments which illustrate by way of example the principles of the invention.

DETAILED DESCRIPTION OF THE PREFERRED EMBODIMENTS

The present invention relates to an anticoagulant which is releasably associated with a cell membrane mimicking substance. Medical devices or components thereof are either directly formed of a biomedical polymer having such material incorporated therein or alternatively coated therewith. Heparin-phosphatidylcholine (HPTC) has been found to be most effective for the purposes of the present invention.

The anticoagulating effect of heparin is well recognized while its natural occurrence in the blood stream renders it biocompatibile. PTC, commonly referred to as lecithin, is a compound of similar compatibility as it is a natural component of cell membranes. PTC is readily incorporated in a variety of polymers to which it imparts a cell membrane-mimicking character by virtue of its lipid structure and characteristic functional groups. Furthermore, PTC functions as a plasticizer in most polymers in which it is incorporated.

By forming a heparin-PTC complex, the heparin is readily incorporated within a polymer via the PTC. Moreover, the relatively weak association of the heparin ligands to the PTC molecule, allow the ligands to become relatively easily disassociated and thereby gradually released. It has been found that HPTC is especially well suited for the purposes of the present invention due to the biocompatibility of both components, the anticoagulating effect of the heparin, the cell mimicking characteristic of the PTC, the compatibility of HPTC with biomedical polymers and the relatively fast release rate of the heparin from the HPTC.

In order to forman anti-thrombogenic film according to the present invention, soybean derived lecithin dissolved in ethyl acetate, was combined with sodium heparin dissolved in water, in a ratio of approximately 4.17:1, by weight of lecithin:heparin. The mixture was then stirred and evaporated to dryness in a water bath to form a homogeneous, and brittle residue, tan in color. The residue was subsequently dissolved in methylchloride, added to polycaprolactone and cast as a film. The resulting film was flexible, extensible, homogeneous, approximately 1.5 to 2.0 mil. thick and tan in color. The final heparin concentration in the film was approximately 5% by weight.

By using similar organic solvent processing methods, an HPTC complex was incorporated in a biodegradable PLLA (poly L-lactic acid) film. It was found that levels of up to over 12% by weight heparin could be suspended in a thin film. However, about 7.5% by weight heparin seemed to be the upper limit for yielding a PLLA film of satisfactory strength.

In order to apply an HPTC containing film to a surface, a number of techniques may be employed. By repeatedly dipping such surface into a solution supporting an HPTC/polymer combination, successive layers are gradually built up until the desired film thickness is achieved. Alternatively, the HPTC containing polymer is first cast and allowed to dry to a film which is then wrapped about the surface to be coated. Subsequent heating of the film wrapped surface causes the film to soften and tightly adhere to the surfaces. It has been found that the latter technique is preferred when the surface to be coated is of a configuration which fails to take on an even coating of a liquid due to the liquid's surface tension. This is especially critical when small diameter bores or orifices must remain clear.

Alternatively, the HPTC complex is directly admixed with a biomedical polymer of which a particular medical device or component thereof is formed. This serves to disperse the anti-thrombogenic material throughout the entire structure. The lecithin to heparin ratio is similarly adjusted to about 4.17:1 by weight as dictated by inherent stoichiometry.

In order to determine the release rate of heparin from a HPTC containing film, 7.4% by weight HPTC in PLLA was applied to slotted tube stents. The coated stents were individually placed into polystyrene test tubes, maintained at constant temperature and continuously shaken. At various time intervals, the incubation media (deionized water) was changed. The concentration of heparin in the changed media was measured via the Azure A method. The net results showed an asymptotic drop in the release rate wherein substantially all of the heparin was released within about a five to six day period.

In testing the antithrombogenic efficacy of material according to the present invention, four groups of stents were prepared; a first group was coated with a film of PLLA, a second group was coated with a 7.4% HPTC containing PLLA film, while a third group was coated with heparin-tridodecylmethylammonium chloride complex (H-TDMAC) containing PLLA film. Uncoated stainless steel stents served as controls and comprised the fourth group. In a double blind study, the stents were placed in conduits through which fresh blood containing $^{111}$Indium labeled platelets was circulated at 37° C. Flow was adjusted to approximately 80 ml/min and sustained for one hour. At the end of the experiment, the stents were rinsed with saline, fixed in buffered glutaraldehyde solution and the radioactivity associated with each stent was determined by gamma counting. Total radioactivity associated with each stent was directly related to the amount of platelet adhesion and therefore provided a quantitative evaluation of one aspect of antithrombogenic activity. Additionally, each stent was examined macroscopically. The results of the experiments showed that although the total amount of platelet aggregation varied significantly, the HPTC/PLLA coated stents were the only stents that remained occlusion free throughout the entire test period. All other stents became occluded within one hour. The results of this experiment suggest that the HPTC containing coating of the present invention provides superior antithrombogenic activity relative to certain prior art systems.

The present invention is applicable to a number of medical devices in addition to expandable intraluminal devices, commonly referred to as stents. Reduced antithrombogenicity is advantageous in any device or surface of such device that comes in contact with blood flow. Such devices include, but are not limited to, intravascular catheters, implantable artificial organs, kidney dialysis machines and heart lung machines.

While a particular form of the invention has been illustrated and described, it will also be apparent to those skilled in the art that various modifications can be made without departing from the spirit and scope of the invention. Accordingly, it is not intended that the invention be limited except by the appended claims.

What is claimed is:

1. An antithrombogenic material comprising:
   heparin, an anticoagulation agent, complexed with phosphatidylcholine, a cell membrane mimicking substance, so as to be releasably associated therewith, incorporated within a biomedical polymer.

2. A biomedical device formed of the antithrombogenic material of claim 1.

3. A biomedical device coated with the antithrombogenic material of claim 1.

4. A stent coated with antithrombogenic material of claim 1.

5. The antithrombogenic material of claim 1 wherein said biomedical polymer is selected from the group consisting of polyurethanes, polyamides, polycarbonates, and polyesters.

6. The antithrombogenic material of claim 1 wherein said biomedical polymer comprises a biodegradable polymer and wherein said material is applied as a film to blood contacting surfaces of a medical device.

7. The antithrombogenic material of claim 6 wherein said biodegradable polymer comprises poly-L-lactic acid (PLLA)

8. A method for imparting antithrombogenic characteristics to a medical device, comprising the steps of:
   forming a solution which supports heparin, an anticoagulation agent, complexed with phosphatidylcholine, a cell membrane mimicking substance, so as to be releasably associated therewith;
   coating preselected surfaces of said medical device with said solution; and
   drying said coating to provide a dry film adhering to said surfaces.

9. The method of claim 8 wherein said solution includes a heparin-phosphatidylcholine complex and poly-L-lactic acid polymer.

10. The method of claim 8 wherein said medical device comprises a stent.

11. A method for imparting antithrombogenic characteristics to a medical device, comprising the steps of:
    forming a dry film containing heparin, an anticoagulation agent, complexed with phosphatidylcholine, a cell mimicking substance, so as to be releasably associated therewith;
    placing said dry film on selected surfaces of said medical device;
    heating said dry film to soften and adhere said film to said surfaces.

12. The method of claim 16 wherein said film further contains a biodegradable polymer.

13. The method of claim 12 wherein said polymer comprises poly-L-lactic acid.

14. A method for producing a medical device having antithrombogenic characteristics, comprising the steps of:
    forming a substance having heparin, an anticoagulation agent complexed with phosphatidylcholine, a cell mimicking compound so as to be releasably associated therewith;
    intimately admixing said substance with a structural polymer; and
    forming said medical device with said admixture.

* * * * *